(12) United States Patent
White et al.

(10) Patent No.: US 8,465,517 B2
(45) Date of Patent: Jun. 18, 2013

(54) FLEXIBLE TAMPING DEVICE

(75) Inventors: John White, Lakeville, MN (US);
Andrew Thomas Forsberg, Minneapolis, MN (US)

(73) Assignee: St. Jude Medical Puerto Rico LLC, Caguas, PR (US)

( * ) Notice: Subject to any disclaimer, the term of this patent is extended or adjusted under 35 U.S.C. 154(b) by 420 days.

(21) Appl. No.: 12/789,284

(22) Filed: May 27, 2010

(65) Prior Publication Data
US 2010/0234883 A1 Sep. 16, 2010

Related U.S. Application Data

(62) Division of application No. 11/532,819, filed on Sep. 18, 2006, now Pat. No. 7,749,248.

(51) Int. Cl.
*A61B 17/08* (2006.01)

(52) U.S. Cl.
USPC ............................................. 606/213

(58) Field of Classification Search
USPC ............. 606/93–95, 139, 142, 144, 200, 213, 606/215, 216, 221, 232; 623/2.11, 2.13; 600/7
See application file for complete search history.

(56) References Cited

U.S. PATENT DOCUMENTS

| | | | |
|---|---|---|---|
| 4,317,445 A | 3/1982 | Robinson | |
| 4,852,568 A | 8/1989 | Kensey | |
| 4,890,612 A | 1/1990 | Kensey | |
| 5,021,059 A | 6/1991 | Kensey et al. | |
| 5,061,274 A | 10/1991 | Kensey | |
| 5,192,302 A | 3/1993 | Kensey et al. | |
| 5,222,974 A | 6/1993 | Kensey et al. | |
| 5,290,310 A | 3/1994 | Makower et al. | |
| 5,292,332 A | 3/1994 | Lee | |
| 5,306,254 A | 4/1994 | Nash et al. | |
| 5,312,435 A | 5/1994 | Nash et al. | |
| 5,320,639 A | 6/1994 | Rudnick | |
| 5,324,306 A | 6/1994 | Makower et al. | |
| 5,326,350 A | 7/1994 | Li | |
| 5,342,393 A | 8/1994 | Stack | |
| 5,383,897 A | 1/1995 | Wholey | |
| 5,383,899 A | 1/1995 | Hammerslag | |
| RE34,866 E | 2/1995 | Kensey et al. | |
| 5,403,329 A | 4/1995 | Hinchliffe | |
| 5,405,354 A | 4/1995 | Sarret | |
| 5,411,520 A | 5/1995 | Nash et al. | |
| 5,431,639 A | 7/1995 | Shaw | |
| 5,431,666 A | 7/1995 | Sauer et al. | |
| 5,437,631 A | 8/1995 | Janzen | |
| 5,443,481 A | 8/1995 | Lee | |
| 5,462,561 A | 10/1995 | Voda | |
| 5,486,195 A | 1/1996 | Myers et al. | |
| 5,496,332 A | 3/1996 | Sierra et al. | |

(Continued)

*Primary Examiner* — Corrine M McDermott
*Assistant Examiner* — Alexander Orkin
(74) *Attorney, Agent, or Firm* — Holland & Hart LLP

(57) ABSTRACT

A method and apparatus for sealing a puncture or incision formed percutaneously in tissue separating two internal portions of the body of a living being with an anchor, a sealing plug and a filament connecting the anchor and sealing plug. The method and apparatus provide for a tamping device that is coilable in some configurations and stiff and straight in other configurations. The coilable tamping device may also automatically tamp the sealing plug when the apparatus is withdrawn from the puncture site. The automatic uncoiling and tamping is facilitated by transducing a motive force generated by the withdrawal of the apparatus into a tamping force.

27 Claims, 10 Drawing Sheets

U.S. PATENT DOCUMENTS

| | | |
|---|---|---|
| 5,507,744 A | 4/1996 | Tay et al. |
| 5,531,759 A | 7/1996 | Kensey et al. |
| 5,545,178 A | 8/1996 | Kensey et al. |
| 5,571,181 A | 11/1996 | Li |
| 5,601,603 A | 2/1997 | Illi |
| 5,613,974 A | 3/1997 | Andreas et al. |
| 5,626,588 A | 5/1997 | Sauer et al. |
| 5,643,318 A | 7/1997 | Tsukernik et al. |
| 5,645,566 A | 7/1997 | Brenneman et al. |
| 5,649,959 A | 7/1997 | Hannam et al. |
| 5,662,663 A | 9/1997 | Shallman |
| 5,662,681 A | 9/1997 | Nash et al. |
| 5,665,107 A | 9/1997 | Hammerslag |
| 5,674,231 A | 10/1997 | Green et al. |
| 5,700,277 A | 12/1997 | Nash et al. |
| 5,716,375 A | 2/1998 | Fowler |
| 5,725,551 A | 3/1998 | Myers et al. |
| 5,728,114 A | 3/1998 | Evans et al. |
| 5,728,122 A | 3/1998 | Leschinsky et al. |
| 5,728,132 A | 3/1998 | Van Tassel et al. |
| 5,728,134 A | 3/1998 | Barak |
| 5,755,727 A | 5/1998 | Kontos |
| 5,759,194 A | 6/1998 | Hammerslag |
| 5,766,183 A | 6/1998 | Sauer |
| 5,766,206 A | 6/1998 | Wijkamp et al. |
| 5,779,719 A | 7/1998 | Klein et al. |
| 5,792,173 A | 8/1998 | Breen et al. |
| 5,810,810 A | 9/1998 | Tay et al. |
| 5,810,846 A | 9/1998 | Virnich et al. |
| 5,810,850 A | 9/1998 | Hathaway et al. |
| 5,810,884 A | 9/1998 | Kim |
| 5,814,065 A | 9/1998 | Diaz |
| 5,820,631 A | 10/1998 | Nobles |
| 5,843,124 A | 12/1998 | Hammerslag |
| 5,853,421 A | 12/1998 | Leschinsky et al. |
| 5,855,585 A | 1/1999 | Kontos |
| 5,860,990 A | 1/1999 | Nobles et al. |
| 5,860,991 A | 1/1999 | Klein et al. |
| 5,868,762 A | 2/1999 | Cragg et al. |
| 5,868,778 A | 2/1999 | Gershony et al. |
| 5,876,411 A | 3/1999 | Kontos |
| 5,906,631 A | 5/1999 | Imran |
| 5,910,155 A | 6/1999 | Ratcliff et al. |
| 5,916,236 A | 6/1999 | Muijs Van de Moer et al. |
| 5,919,207 A | 7/1999 | Taheri |
| 5,921,994 A | 7/1999 | Andreas et al. |
| 5,928,266 A | 7/1999 | Kontos |
| 5,941,897 A | 8/1999 | Myers |
| 5,948,425 A | 9/1999 | Janzen et al. |
| 5,964,782 A | 10/1999 | Lafontaine et al. |
| 5,976,161 A | 11/1999 | Kirsch et al. |
| 5,980,539 A | 11/1999 | Kontos |
| 5,984,950 A | 11/1999 | Cragg et al. |
| 5,997,555 A | 12/1999 | Kontos |
| 6,001,109 A | 12/1999 | Kontos |
| 6,007,562 A | 12/1999 | Harren et al. |
| 6,017,359 A | 1/2000 | Gershony et al. |
| 6,022,372 A | 2/2000 | Kontos |
| 6,024,747 A | 2/2000 | Kontos |
| 6,033,401 A | 3/2000 | Edwards et al. |
| 6,033,427 A | 3/2000 | Lee |
| 6,036,721 A | 3/2000 | Harren et al. |
| 6,042,601 A | 3/2000 | Smith |
| 6,048,357 A | 4/2000 | Kontos |
| 6,048,358 A | 4/2000 | Barak |
| 6,063,085 A | 5/2000 | Tay et al. |
| 6,071,300 A | 6/2000 | Brenneman et al. |
| 6,077,276 A | 6/2000 | Kontos |
| 6,077,279 A | 6/2000 | Kontos |
| 6,110,184 A | 8/2000 | Weadock |
| 6,117,145 A | 9/2000 | Wood et al. |
| 6,120,524 A | 9/2000 | Taheri |
| 6,126,675 A | 10/2000 | Shchervinsky et al. |
| 6,136,010 A | 10/2000 | Modesitt et al. |
| 6,139,556 A | 10/2000 | Kontos |
| 6,162,192 A | 12/2000 | Cragg et al. |
| 6,174,322 B1 | 1/2001 | Schneidt |
| 6,179,863 B1 | 1/2001 | Kensey et al. |
| 6,183,485 B1 | 2/2001 | Thomason et al. |
| 6,183,496 B1 | 2/2001 | Urbanski |
| 6,190,400 B1 | 2/2001 | Van De Moer et al. |
| 6,197,042 B1 | 3/2001 | Ginn et al. |
| 6,206,893 B1 | 3/2001 | Klein et al. |
| 6,231,561 B1 | 5/2001 | Frazier et al. |
| 6,425,911 B1 | 7/2002 | Akerfeldt et al. |
| 6,508,828 B1 | 1/2003 | Akerfeldt et al. |
| 6,547,806 B1 | 4/2003 | Ding |
| 6,569,185 B2 | 5/2003 | Ungs |
| 6,596,014 B2 | 7/2003 | Levinson et al. |
| 6,682,489 B2 | 1/2004 | Tenerz et al. |
| 6,712,837 B2 | 3/2004 | Akerfeldt et al. |
| 6,786,915 B2 | 9/2004 | Akerfeldt et al. |
| 6,837,844 B1 * | 1/2005 | Ellard et al. ................. 600/7 |
| 6,860,895 B1 | 3/2005 | Akerfeldt et al. |
| 2005/0085851 A1 | 4/2005 | Fiehler et al. |
| 2005/0154417 A1 * | 7/2005 | Sepetka et al. ............. 606/200 |
| 2006/0229673 A1 | 10/2006 | Forsberg |
| 2006/0229674 A1 | 10/2006 | Forsberg |
| 2006/0271097 A1 * | 11/2006 | Ramzipoor et al. ......... 606/200 |

* cited by examiner

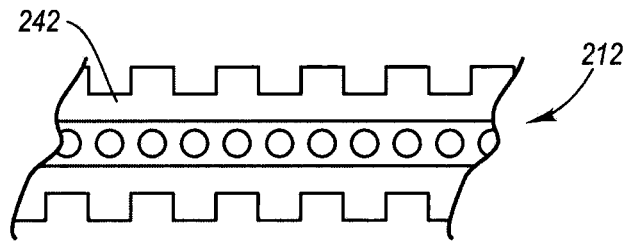
*Fig. 8A*
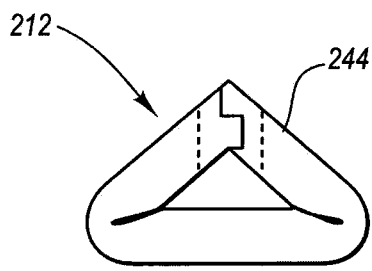
*Fig. 8B*
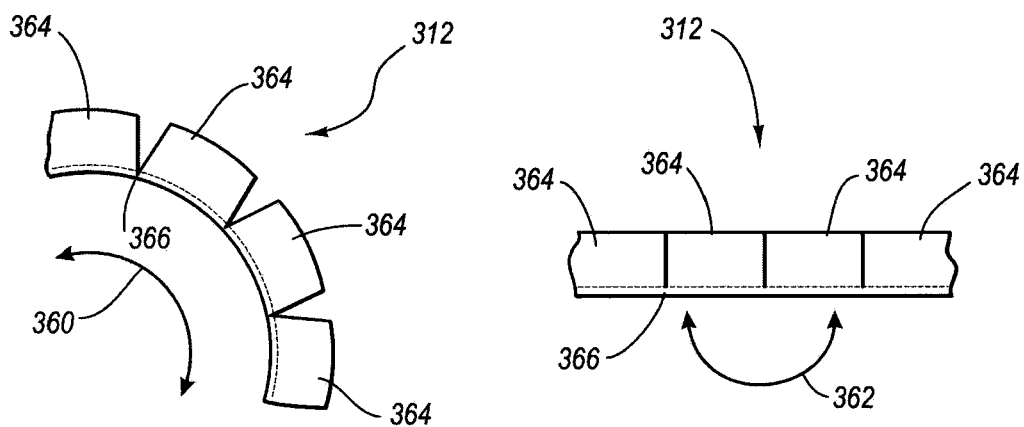
*Fig. 9A*  *Fig. 9B*

FLEXIBLE TAMPING DEVICE

RELATED APPLICATION

This is a divisional of U.S. application Ser. No. 11/532,819 filed on 18 Sep. 2006, now U.S. Pat. No. 7,749,248, the disclosure of which is incorporated, in its entirety, by this reference.

FIELD OF THE INVENTION

This invention relates generally to medical devices and more particularly to devices for sealing punctures or incisions in an internal tissue wall.

BACKGROUND

Various surgical procedures are routinely carried out intravascularly or intraluminally. For example, in the treatment of vascular disease, such as arteriosclerosis, it is a common practice to invade the artery and insert an instrument (e.g., a balloon or other type of catheter) to carry out a procedure within the artery. Such procedures usually involve the percutaneous puncture of the artery so that an insertion sheath can be placed in the artery. The insertion sheath enables the introduction of other instruments (e.g., a catheter) to an operative position within the vascular system. Intravascular and intraluminal procedures unavoidably present the problem of stopping the bleeding at the percutaneous puncture after the procedure has been completed and after the instrument (and any insertion sheaths used therewith) has been removed. Bleeding from puncture sites, particularly in the case of femoral arterial punctures, is typically stopped by utilizing vascular closure devices, such as those described in U.S. Pat. Nos. 6,179,863; 6,090,130; and 6,045,569, which are hereby incorporated by this reference.

Typical closure devices such as the ones described in the above-mentioned patents place a sealing plug at the tissue puncture site. Successful deployment of the sealing plug, however, requires that it be manually ejected from within a device sheath and tamped down to an outer surface of the tissue puncture using a tamping tube. The tamping procedure cannot commence until the device sheath (within which the tamping tube is located) has been removed so as to expose the tamping tube for manual grasping. Under certain conditions, removal of the sheath prior to tamping the sealing plug may cause the sealing plug itself to be retracted from the tissue puncture, hindering subsequent placement of the sealing plug, and resulting in only a partial seal and associated bleeding from the tissue puncture. Accordingly, there is a need to improve the mechanism for deployment of the sealing plug at the site of a tissue puncture.

SUMMARY

In one of many possible embodiments, the present invention provides a tissue puncture closure device for partial insertion into and sealing of an internal tissue wall puncture. The closure device includes a filament extending from a first end of the closure device to a second end of the closure device, an anchor for insertion through the tissue wall puncture attached to the filament at the second end of the closure device, a sealing plug slidingly attached to the filament adjacent to the anchor, and an at least partially coiled tamping device adjacent to the sealing plug for advancing the sealing plug toward the anchor. The tissue puncture closure device may include a spool at the first end, such that a portion of the tamping device coiled on the spool is flexible and folded flat in cross-section, and a portion of the tamping device adjacent to the sealing plug is stiff and comprises a trough. A shaper disposed at the first end may fold the portion of the tamping device coiled on the spool into the stiff trough configuration as it is advanced distally therethrough. According to other embodiments, the shaper longitudinally folds the portion of the tamping device coiled on the spool into a closed polygonal shape as it advances distally therethrough.

According to some aspects of the invention the tamping device comprises a first longitudinal section at least partially coiled on a first spool and a second longitudinal section at least partially coiled on a second spool. The shaper then integrates the first longitudinal section of the tamping device coiled on the first spool and the second longitudinal section of the tamping device coiled on the second spool into a stiff, generally straight member. Accordingly, each of the first and second longitudinal sections may comprise semi-circles in cross-section.

According to some aspects of the invention the tamping device includes a chain that is flexible in a first coiling direction but rigid in a direction opposite of the first coiling direction. For example, the chain may be flexible if coiled in a clockwise direction, but rigid against coiling in a counterclockwise direction. The chain may include a plurality of blocks, each block flexibly linked at one corner to a neighboring block.

According to some aspects of the invention there is an automatic uncoiling device for uncoiling the tamping device in response to retraction of the tissue puncture closure device from a tissue puncture. The automatic uncoiling device may include a spool with a portion of the filament wound thereon, and a gear engaged with the spool.

Another embodiment of the invention provides a medical apparatus including a carrier tube, a handle attached to a first end of the carrier tube, a filament extending between the first end of the carrier tube and a second end of the carrier tube, an anchor attached to the filament at the second end of the carrier tube, a sealing plug slidingly attached to the filament proximal of the anchor, and a tamping device disposed about the filament for driving the sealing plug along the filament distally towards the anchor. According to this embodiment, at least a portion of the tamping device may be coiled within the handle. Moreover, the tamping device may extend through a shaper such that a portion of the tamping device proximal of the shaper comprises a curved, flexible configuration and a portion of the tamping device distal of the shaper comprises a straight, stiff configuration. The apparatus, including the filament and a filament storage spool may comprise a driving mechanism for advancing the tamping device toward the second end in response to a separation force between the anchor and the handle.

According to another embodiment there is a tissue puncture closure device for partial insertion into and sealing of an internal tissue wall puncture accessible through a percutaneous incision, where the closure device comprises a filament connected at a distal end to an anchor and to a sealing plug located proximal of the anchor for disposition and anchoring about the tissue wall puncture, where the improvement comprises means for automatically driving the sealing plug along the filament in a distal direction towards the anchor simultaneously upon withdrawal of the closure device from the tissue wall puncture and means for folding the means for automatically driving from a flexible coiled configuration to a straight, stiff configuration.

Another aspect of the invention provides a method of making an internal tissue puncture sealing device by providing a carrier tube, attaching a handle at a first end of the carrier tube, extending a filament between the first end of the carrier tube and a second end of the carrier tube, attaching an anchor to the filament at the second end of the carrier tube, slidingly attaching a sealing plug to the filament proximal of the anchor, disposing a tamping device about the filament, and coiling at least a portion of the tamping device in the handle. According to some embodiments the coiling comprises wrapping two components of the tamping device around two separate spools.

Another aspect provides a method of sealing a tissue puncture in an internal tissue wall accessible through a percutaneous incision. The method may include withdrawing a closure device from the tissue puncture, and automatically uncoiling a tamping device to tamp a sealing plug at the tissue puncture by transducing a motive force generated by withdrawal of the closure device in a first direction to a tamping force in a second direction. The automatic uncoiling further may include passing the tamping device through a shaper and altering a cross-sectional shape of the tamping device, for example, to stiffen the tamping device. The transducing may include automatically unwinding a filament from a filament spool by deploying an anchor attached to the filament inside the tissue puncture prior to withdrawing the closure device from the tissue puncture.

BRIEF DESCRIPTION OF THE DRAWINGS

The accompanying drawings illustrate various embodiments of the present invention and are a part of the specification. The illustrated embodiments are merely examples of the present invention and do not limit the scope of the invention.

FIG. 8A is a top view of another alternative tamping device shown in FIG. 5 according to one embodiment of the present invention.

FIG. 8B is an enlarged cross-section view of the alternative tamping device shown in FIG. 8A taken along the line B-B of the tamping device shown in FIG. 5 according to one embodiment of the present invention.

FIG. 9A is an enlarged side-view of a coiled portion of a tamping device for use with the tissue puncture closure device of FIG. 5 according to another embodiment of the present invention.

FIG. 9B is an enlarged side-view of an uncoiled portion of the tamping device shown in FIG. 9A according to one embodiment of the present invention.

Throughout the drawings, identical reference numbers designate similar, but not necessarily identical, elements.

DETAILED DESCRIPTION

Figure 1:
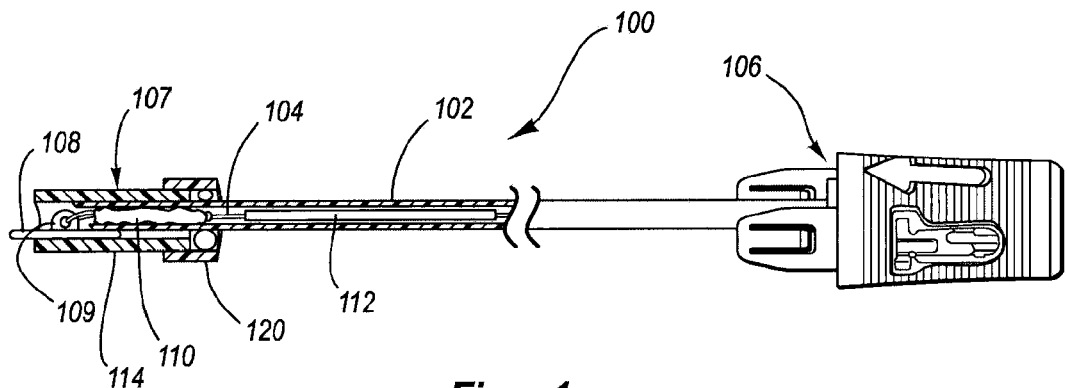
FIG. 1 is a side view, partly in section, of an internal tissue puncture closure device according to the prior art.

As mentioned above, vascular procedures are conducted throughout the world and require access to an artery through a puncture. Most often, the artery is a femoral artery. To close the puncture following completion of the procedure, many times a closure device is used to sandwich the puncture between an anchor and a sealing plug. However, sometimes the sealing plug is not properly seated against an exterior situs of the arteriotomy. If the plug does not seat against the arteriotomy, there is a potential for elongated bleeding. The present invention describes methods and apparatus to reduce or eliminate movement or misplacement of the sealing plug with a compact device. While the vascular instruments shown and described below include insertion sheaths and puncture sealing devices, the application of principles described herein are not limited to the specific devices shown. The principles described herein may be used with any vascular closure device. Therefore, while the description below is directed primarily to arterial procedures and certain embodiments of a vascular closure device, the methods and apparatus are only limited by the appended claims.

As used throughout the claims and specification the term "tamp" or "tamping" is used broadly to mean pushing or packing by one or a succession of pushes, blows, or taps, but not by excessive force. The term "effecting" means producing an outcome, achieving a result, or bringing about. "Coiled" means rings formed by winding, and includes partial windings and arcs. An "arc" is something shaped like a curve or arch, including a segment of a circle or ellipse. A "spool" is a cylinder or other device on which something else is at least partially wound. A "lumen" refers to any open space or cavity in a bodily organ, especially in a blood vessel. A "shaper" is any device that changes the cross-sectional shape, bending moment, or linearity of another device. The words "including" and "having," as used in the specification, including the claims, have the same meaning as the word "comprising."

Referring now to the drawings, and in particular to FIGS. 1-4, a vascular puncture closure device 100 is shown according to the prior art. The vascular puncture closure device 100 includes a carrier tube 102 with a filament or suture 104 extending at least partially therethrough. The closure device also includes a first or proximal end 106 and a second or distal end 107. External to a second or distal end 107 of the carrier tube 102 is an anchor 108. The anchor is an elongated, stiff, low profile member including an eye 109 formed at the middle. The anchor 108 is typically made of a biologically resorbable polymer.

The suture 104 is threaded through the anchor 108 and back to a collagen pad 110. The collagen pad 110 may be comprised of randomly oriented fibrous material bound together by chemical means. The collagen pad 110 is slidingly attached to the suture 104 as the suture passes distally through the carrier tube 102, but as the suture traverses the anchor 108 and reenters the carrier tube 102, it is securely slip knotted proximal to the collagen pad 110 to facilitate cinching of the collagen pad 110 when the closure device 100 is properly placed and the anchor 108 deployed (see FIG. 4).

The carrier tube 102 typically includes a tamping tube 112 disposed therein. The tamping tube 112 is slidingly mounted on the suture 104 and may be used by an operator to tamp the collagen pad 110 toward the anchor 108 at an appropriate time to seal a percutaneous tissue puncture. Prior to deployment of the anchor 108 within an artery, the eye 109 of the anchor 108 rests outside the distal end 107 of the carrier tube 102. The anchor 108 may be temporarily held in place flush with the carrier tube 102 by a bypass tube 114 disposed over the distal end 107 of the carrier tube 102.

Figure 2:
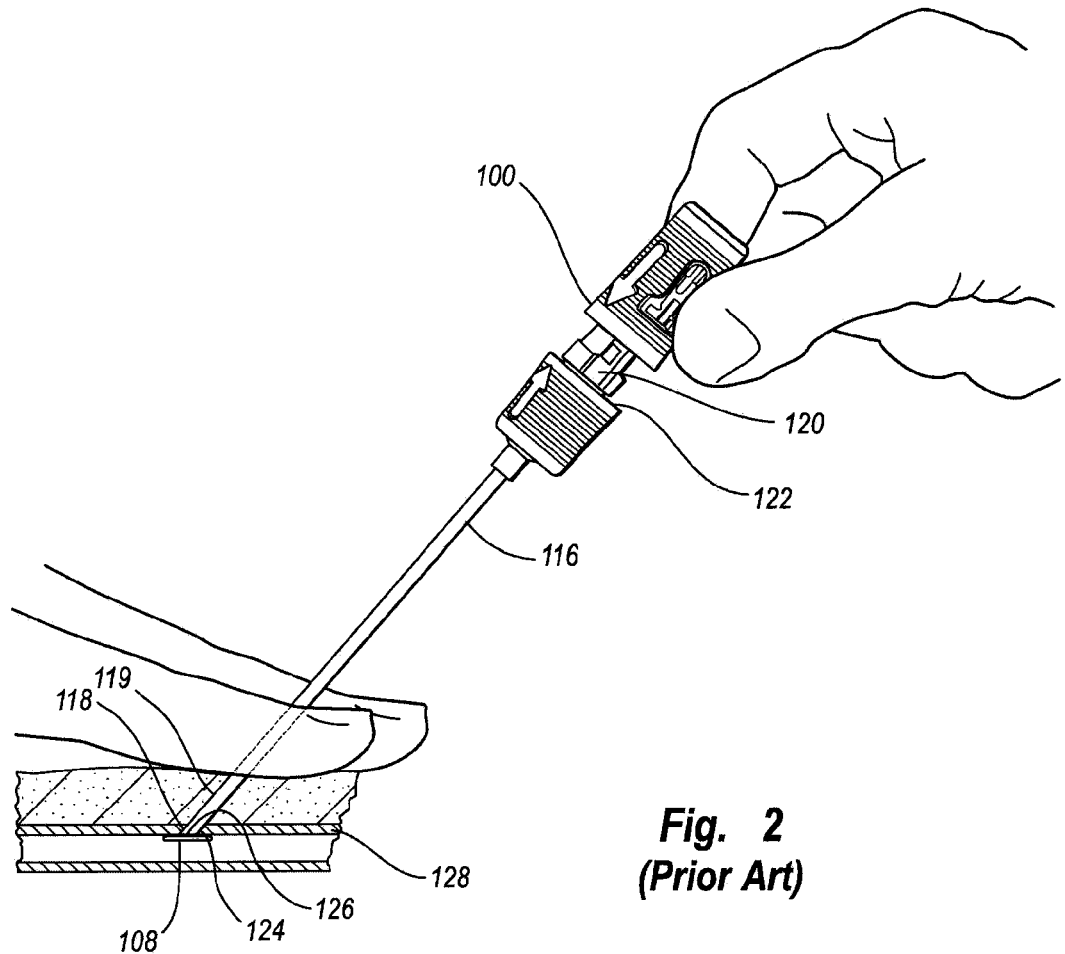
FIG. 2 is a side view of the tissue puncture closure device of FIG. 1 inserted through an insertion sheath and engaged with an artery, the artery shown in section, according to the prior art.
Figure 3:
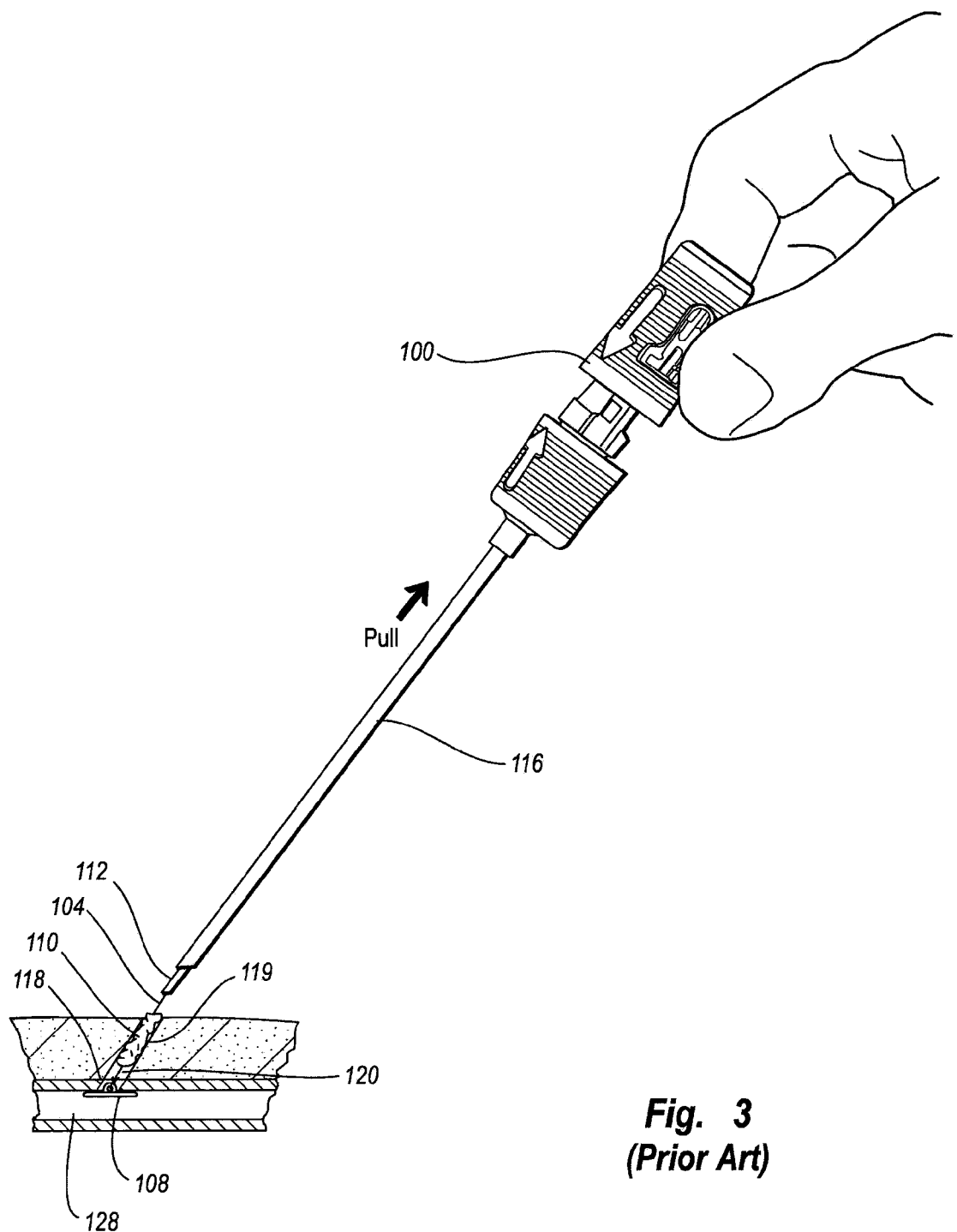
FIG. 3 is a side view of the tissue puncture closure device, insertion sheath, and artery of FIG. 2, wherein the tissue closure device and insertion sheath are being withdrawn from the artery to deploy a collagen pad according to the prior art.
Figure 4:
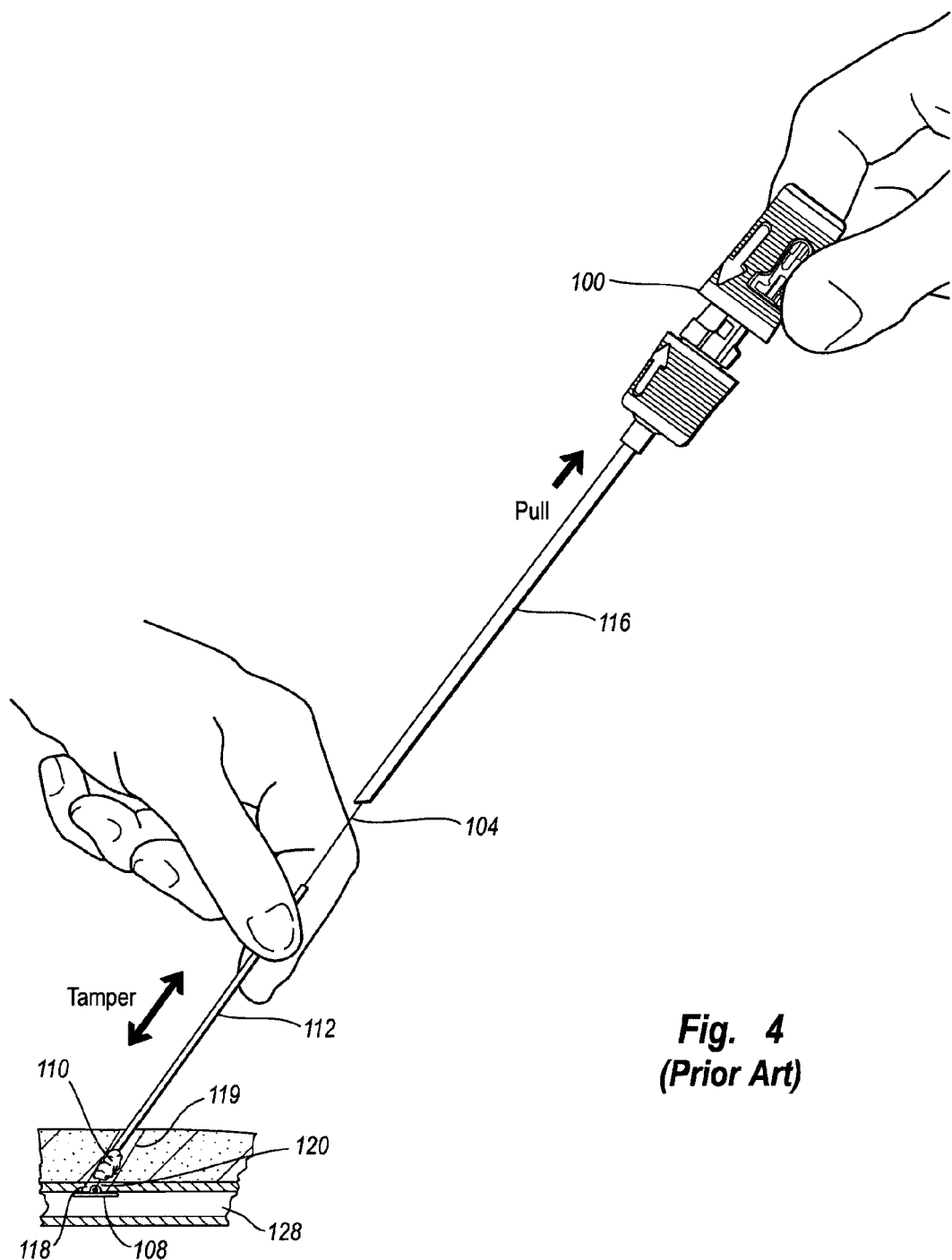
FIG. 4 is a side view of the tissue puncture closure device, insertion sheath, and artery shown in FIG. 3 with a tamping tube fully exposed and being used to tamp the collagen pad according to the prior art.

The flush arrangement of the anchor 108 and carrier tube 102 allows the anchor 108 to be inserted into an insertion sheath 116 as shown in FIGS. 2-4, and eventually through an arterial puncture 118. The insertion sheath 116 is shown in FIGS. 2-4 inserted through a percutaneous incision 119 and into an artery 128. However, the bypass tube 114 (FIG. 1) includes an oversized head 120 that prevents the bypass tube 114 from passing through an internal passage of the insertion sheath 116. Therefore, as the puncture closure device 100 is inserted into the insertion sheath 116, the oversized head 120 bears against a surface 122 of insertion sheath 116. Further insertion of the puncture closure device 100 results in sliding movement between the carrier tube 102 (FIG. 1) and the bypass tube 114, releasing the anchor 108 from the bypass tube 114 (FIG. 1). However, the anchor 108 remains in the flush arrangement shown in FIG. 1 following release from the bypass tube 114, limited in movement by the insertion sheath 116.

The insertion sheath 116 includes a monofold 124 at a second or distal end 126 thereof. The monofold 124 acts as a one-way valve to the anchor 108. The monofold 124 is a plastic deformation in a portion of the insertion sheath 116 that elastically flexes as the anchor 108 is pushed out through the distal end 126 of the insertion sheath 116. Typically, after the anchor 108 passes through the distal end 126 of the insertion sheath 116 and enters the artery 128, the anchor 108 is no longer constrained to the flush arrangement with respect to the carrier tube 102 and it deploys and rotates to the position shown in FIG. 2.

Referring next to FIGS. 3-4, with the anchor 108 deployed, the puncture closure device 100 and the insertion sheath 116 are withdrawn together, depositing the collagen pad 110 in the incision tract 119 and exposing the tamping tube 112. With the tamping tube 112 fully exposed as shown in FIG. 4, the collagen pad 110 is manually tamped, and the anchor 108 and collagen pad 110 are cinched together and held in place with a self-tightening slip-knot on the suture 102. Thus, the tissue puncture is sandwiched between the anchor 108 and the collagen pad 110, thereby sealing the tissue puncture 118. The suture 104 is then cut and the puncture 118 may be closed. The suture 104, anchor 108, and collagen pad 110 are generally made of resorbable materials and therefore remain in place while the puncture 118 heals.

Using the typical tissue puncture closure device 100 described above, however, the tamping of the collagen pad 110 cannot commence until the sheath 116 has been removed so as to expose the tamping tube 112 for manual grasping. Under certain conditions, removal of the sheath 116 prior to tamping the collagen pad 110 causes the collagen pad 110 to retract from the tissue puncture 118, creating a gap 120 between the collagen pad 110 and the puncture 118. The gap 120 may remain even after tamping as shown in FIG. 4, and sometimes results in only a partial seal and bleeding from the tissue puncture 118.

Therefore, the present specification describes a tissue puncture closure device with a tamping tube that is at least partially coiled, which may automatically drive a sealing plug (such as collagen pad 110) toward a tissue puncture upon withdrawal of the tissue puncture closure device from the tissue puncture site. While the preferred embodiments of the tissue puncture closure device are shown and described below, the principles of the present specification may be incorporated into any of a number of tissue closure devices. The specific embodiments described below are for illustrative purposes only, and are not limiting.

As described above, the general structure and function of tissue closure devices used for sealing a tissue puncture in an internal tissue wall accessible through an incision in the skin are well known in the art. Applications of closure devices including those implementing principles described herein include closure of a percutaneous puncture or incision in tissue separating two internal portions of a living body, such as punctures or incisions in blood vessels, ducts or lumens, gall bladders, livers, hearts, etc.

Figure 5:
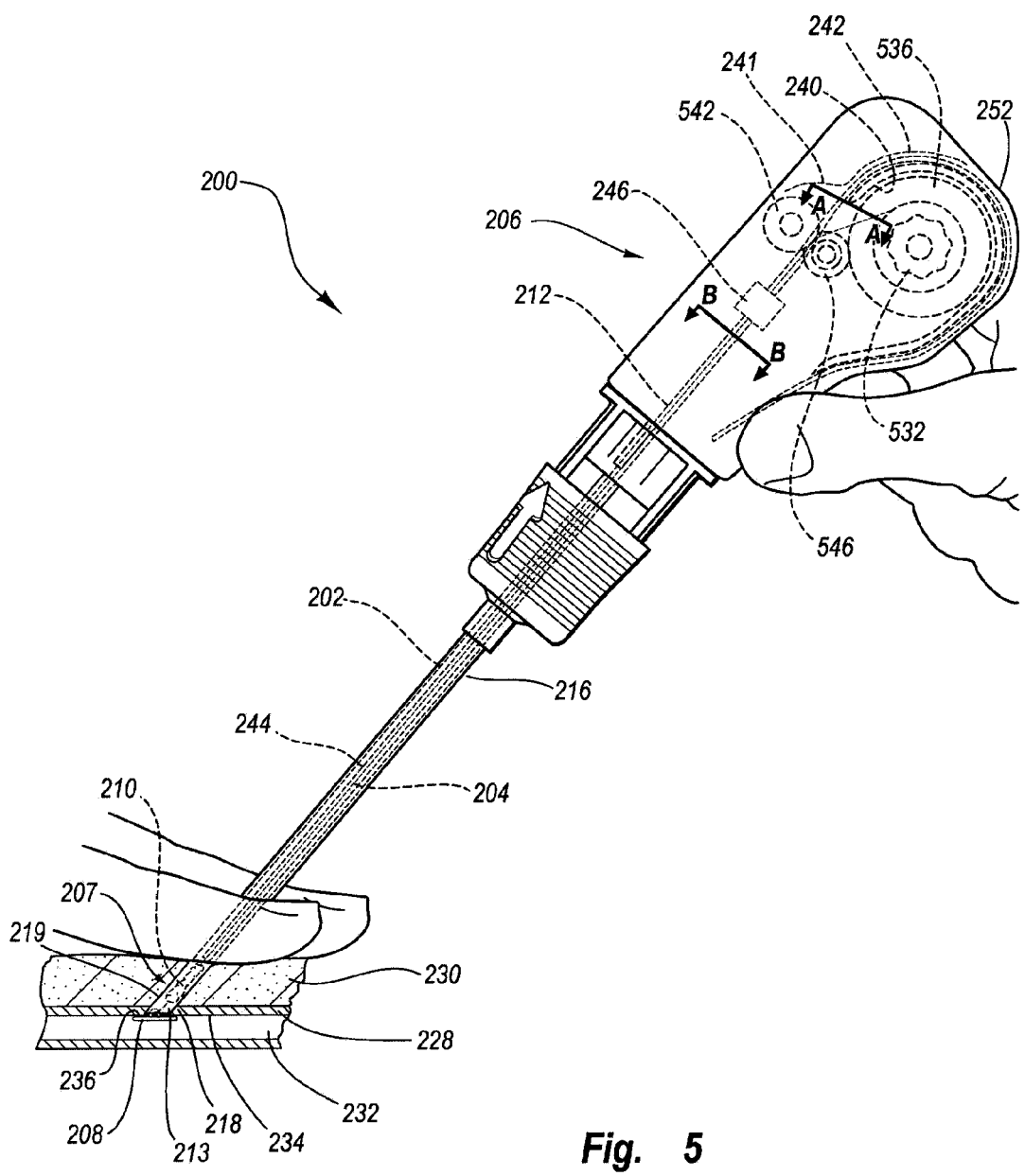
FIG. 5 is a side view of a tissue puncture closure device with an automatic tamping device uncoiling mechanism shown with hidden lines according to one embodiment of the present invention; the tissue closure device is shown engaged with an artery.

Referring now to FIG. 5, a medical apparatus, for example a tissue puncture closure device 200 is shown according to one embodiment of the present invention. The closure device 200 has particular utility when used in connection with intravascular procedures, such as angiographic dye injection, cardiac catheterization, balloon angioplasty and other types of recanalizing of atherosclerotic arteries, etc. as the closure device 200 is designed to cause immediate hemostasis of the blood vessel (e.g., arterial) puncture. However, it will be understood that while the description of the preferred embodiments below are directed to the sealing off of percutaneous punctures in arteries, such devices have much more wide-spread applications and can be used for sealing punctures or incisions in other types of tissue walls as well. Thus, the sealing of a percutaneous puncture in an artery, shown herein, is merely illustrative of one particular use of the tissue closure device 200 of the present invention.

The tissue closure device 200 includes a first or proximal end 206 and a second or distal end 207. A carrier tube 202 extends from the proximal end 206 to the distal end 207 and includes an outlet 213 at the distal end 207. The carrier tube 202 may be made of plastic or other material and is designed for insertion through a sheath 216, which is designed for insertion through a percutaneous incision 219 in a tissue layer 230 and into a lumen 232. According to FIG. 5, the lumen 232 comprises an interior portion of a femoral artery 228.

At the distal end 207 of the carrier tube 202 there is an anchor 208 and a sealing plug 210. The anchor 208 of the present embodiment is an elongated, stiff, low-profile member arranged to be seated inside the artery 228 against an artery wall 234 contiguous with a puncture 218. The anchor 208 is preferably made of a biologically resorbable polymer. The sealing plug 210 is formed of a compressible sponge, foam, or fibrous mat made of a non-hemostatic biologically resorbable material such as collagen, and may be configured in any shape so as to facilitate sealing the tissue puncture 218.

The sealing plug 210 and anchor 208 are connected to one another by a filament or suture 204 that is also biologically resorbable. The anchor 208, the sealing plug 210, and the suture 204 are collectively referred to as the "closure elements" below. As shown in FIG. 5, the anchor 208 is arranged adjacent to and exterior of the distal end 207 of the carrier tube 202, while the sealing plug 210 is initially disposed within carrier tube 202. Although the anchor 208 is shown deployed with a first surface 236 abutting the artery wall 234, it will be understood that initially the anchor is arranged axially along the carrier tube 202 to facilitate insertion into the lumen 232 (see, for example, the anchor 108 of FIG. 1). The suture 204 extends distally from the proximal end 206 of the closure device 200 through the carrier tube 202. The suture 204 is threaded through one or more perforations in the sealing plug 210, through a hole in the anchor 208, and proximally back toward the carrier tube 202 to the sealing plug 210. The suture 204 is preferably threaded again through a perforation or series of perforations in the sealing plug 210. The suture 204 may also be threaded around itself to form a self-tightening slip-knot. The suture 204 thus connects the anchor 208 and the sealing plug 210 in a pulley-like arrangement to cinch the anchor 208 and the sealing plug 210 together when the carrier tube 202 is pulled away from the anchor 208 and the sealing plug 210, sandwiching and locking the anchor and plug together and thereby sealing the tissue puncture 218.

Figure 12:
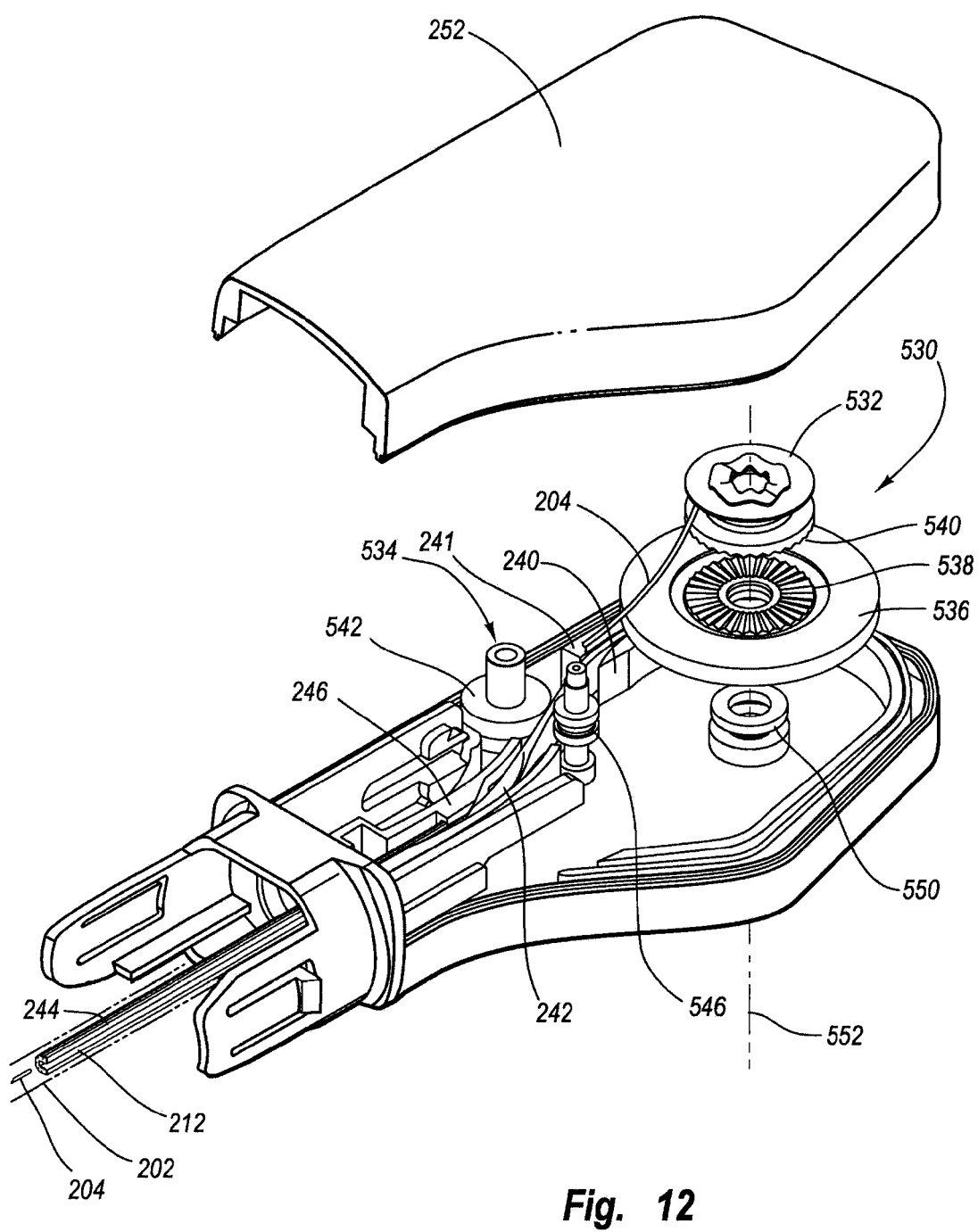
FIG. 12 is an partial assembly view of the tissue puncture closure device of FIG. 5 according to one embodiment of the present invention.

The carrier tube 202 also houses a tamping device, for example the at least partially coiled tamping device 212 shown in FIG. 5, for advancing the sealing plug 210 along the suture 204 and toward the anchor 208. The tamping device 212 is shown with a first portion 242 partially coiled within a handle 252 and a second portion 244 extending distally toward the sealing plug 210. The first portion 242 may be coiled around a spool or arranged in between guides 240, 241 (FIG. 12). The first portion 242 includes a variable length of the tamping device 212 proximal of a shaper 246 and the second portion 244 includes a variable length of the tamping device 212 distal of the shaper 246. The shaper 246 is shown in more detail below with reference to FIG. 12 and may alter a cross-section and/or increase a moment of inertia along certain axes of some embodiments of the tamping device 212 as it passes therethrough. Accordingly, the first portion 242 of the tamping device 212 is generally flexible and therefore coilable in at least one direction, but the second portion 244 is generally stiff and straight.

The tamping device 212 may comprise any number of configurations that enable the first portion 242 to coil and the second portion 244 to straighten and stiffen. The first portion 242 facilitates compaction of the closure device 200 by storing a length of the tamping device 212 in a non-linear coil. The second portion 244 facilitates advancing or tamping the sealing plug 210 toward the anchor 208. Several examples of different configurations of the tamping device 212 are shown and described below with reference to FIGS. 6A-10B.

Figure 6A:
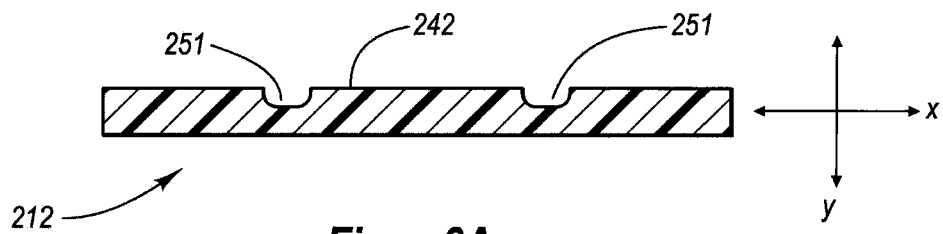
FIG. 6A is an enlarged cross-sectional view taken along the line A-A of the tamping device shown in FIG. 5 according to one embodiment of the present invention.
Figure 6B:
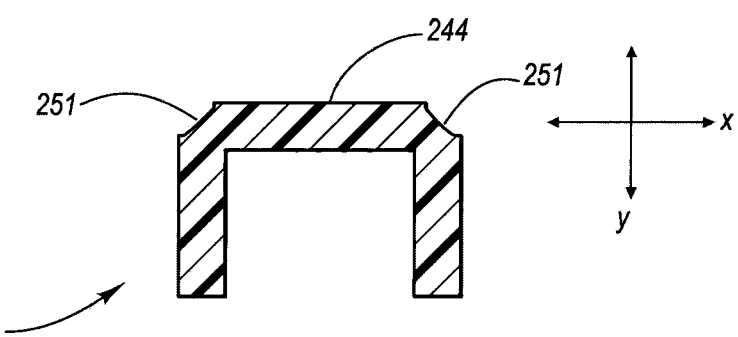
FIG. 6B is an enlarged cross-sectional view taken along the line B-B of the tamping device shown in FIG. 5 according to one embodiment of the present invention.

Referring to FIGS. 6A-6B, one embodiment of the tamping device 212 is shown according to principles of the present invention. According to FIG. 6A, which is a cross sectional view of the tamping device 212 taken along line A-A of FIG. 5, the first portion 242 of the tamping device comprises a generally open, flat cross-section. The generally flat cross section of the first portion 242 of the tamping device 212 has a generally low moment of inertia about an X-axis and therefore provides for flexibility about the X-axis of the tamping device 212. The tamping device 212 as shown in FIG. 6A may include a pair of notches 251 which weaken the structure and that facilitate folding or bending the tamping device into a different cross-sectional configuration.

According to the embodiment of FIGS. 6A-6B, as the first portion 242 of the tamping device 212 passes through the stationary shaper 246 (FIG. 5), it is folded to form a different cross-sectional as shape shown in FIG. 6B. FIG. 6B represents a cross sectional view of the tamping device 212 taken along line B-B of FIG. 5. Accordingly, FIG. 6B represents the cross section of the second portion 244 of the tamping device 212. As shown in FIG. 6B, the tamping device 212 is folded to form a trough, or a general U or V-shape. Accordingly, the shaper 246 (FIG. 5) may comprise wedge surfaces forming a trough. The trough-shape formed in the second portion 244 of the tamping device 212 has a much higher moment of inertia about the X-axis and is therefore much more stiff, rigid, and straight as compared to the flat configuration of the first portion 242 (FIG. 6A). Therefore, the second portion 244 of the tamping device is well suited for bearing against and tamping the sealing plug 210 (FIG. 5) toward the anchor 208 (FIG. 5). The folding of the tamping device between flexible and stiff configurations as shown in FIGS. 6A-6B facilitates a compact closure device 200 by allowing a sufficient length of the tamping device 212 to be coiled within the handle 252 of the closure device 200, and also provides adequate stiffness to the tamping device 212 at the sealing plug 210 (FIG. 5).

Figure 7A:
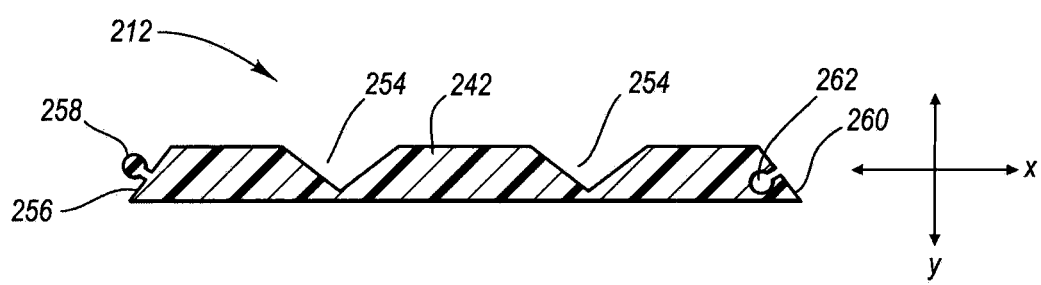
FIG. 7A is an enlarged cross-sectional view of an alternative tamping device taken along the line A-A of the tamping device shown in FIG. 5 according to one embodiment of the present invention.
Figure 7B:
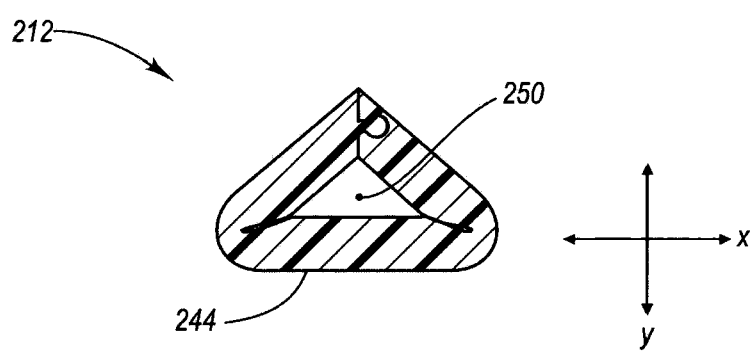
FIG. 7B is an enlarged cross-sectional view of the alternative tamping device shown in FIG. 7A, taken along line B-B of the tamping device shown in FIG. 5 according to one embodiment of the present invention.

Another embodiment of the tamping device 212 is shown in cross-section in FIGS. 7A-7B. Similar to the configuration shown in FIG. 6A, the embodiment of FIG. 7A illustrates a cross section taken along line A-A of FIG. 5 of the first portion 242 of the tamping device 212. The first portion 242 is arranged in a generally open, flexible, flat configuration that allows the first portion 242 to be conveniently coiled. The tamping device 212 of FIGS. 7A-7B, however, includes a two or more notches 254 that facilitate folding the tamping device 212 into a closed polygonal shape. In addition, a first edge 256 of the tamping device 212 may include a protrusion 258 and a second edge 260 may include a mating cavity 262 that provides a snap-lock geometry for the tamping device 212 when folded. For example, as shown in FIG. 7B, which is a cross section of the second portion 244 of the tamping device 212 taken along line B-B of FIG. 5, the second portion 244 of the tamping device 212 may be folded by the shaper 246 (FIG. 5) into a triangular shape. As with the trough-shape of FIG. 6B, the triangular shape of FIG. 7B has a much higher moment of inertia about the X-axis and is therefore much stiffer in directions transverse to its longitudinal axis 250 than the flat configuration of FIG. 7A. Those of skill in the art having the benefit of this disclosure will understand that other closed polygonal shapes may also be formed from a generally flat configuration by the shaper 246 (FIG. 5) and that the triangular shape is merely exemplary. The shaper 246 (FIG. 5) may include various wedges or surfaces to fold the tamping device 212 into any desirable configuration as it passes therethrough.

Other embodiments may be used as well. For example, the embodiment of FIGS. 8A-8B illustrates another configuration for the tamping device 212 that may be folded between flexible and stiff arrangements. FIG. 8A illustrates a top view of the first portion 242 of FIG. 5 and is generally flat therefore coilable, with toothed edges that engage when folded to stiffen the tamping device 212 and prevent edge sliding. Following folding by the shaper 246 (FIG. 5), the toothed edges engage to form a closed polygon in cross-section, such as the triangle shown in FIG. 8B, which illustrates the second portion 244 of the tamping device 212 taken along line B-B of FIG. 5.

However, instead of using the shaper 246 to alter the cross section of the tamping device 212 shown in FIG. 5, some embodiments of the tamping device 212 may be coilable in one direction and stiff in other directions without any folding or changing of the cross section. Accordingly, some embodiments of the closure device 200 may not include the shaper 246. For example, the tamping device may comprise a chain 312 as shown in FIGS. 9A-9B. FIGS. 9A-9B illustrate the chain 312 from a side view rather than a cross-sectional view. The chain 312 is flexible in a first direction represented by an arced arrow 360 in FIG. 9A, but rigid in other directions including a second direction represented by a second arced arrow 362 shown in FIG. 9B.

The chain 312 as shown in FIGS. 9A-9B includes a plurality of blocks 364 flexibly linked together. Each of the blocks 364 is connected to a neighboring block at one corner by a flexible member 366. The flexible member 366 may comprise a plastic sheet or some other material that is easily bent. As shown in FIGS. 9A-9B, the chain 312 may be coiled in the first direction 360 within the handle 252 (FIG. 5), but the blocks 364 bear against and interfere with one another to prevent coiling in other directions. Further, the chain 312 may be biased by the flexible member 366 in the second direction 362 so that as the chain 312 is uncoiled, it tends to form the straight, rigid shape illustrated in FIG. 9B. The straight, rigid shape of FIG. 9B provides an effective tamping device for advancing the sealing plug 210 (FIG. 5) toward the anchor 208 (FIG. 5) along the suture 204 (FIG. 5).

Figure 10A:
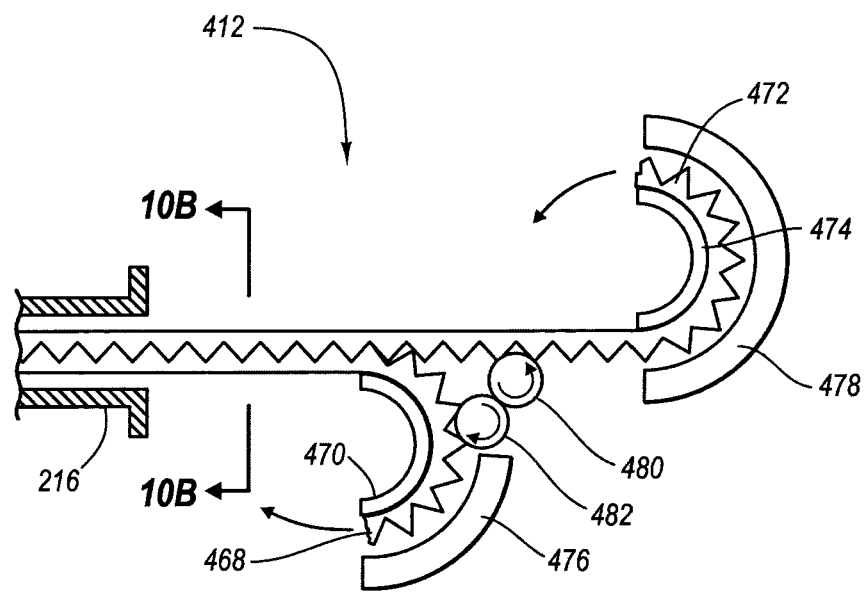
FIG. 10A is a side-view, partly in section, of a tissue puncture closure device with a multi-part tamping device according to another embodiment of the present invention.
Figure 10B:
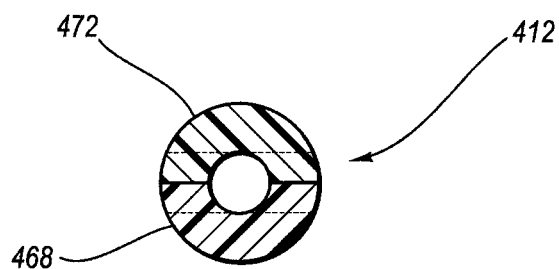
FIG. 10B is an enlarged cross-sectional view taken along the line 10B-10B of the tamping device shown in FIG. 10A according to one embodiment of the present invention.

Moreover, according to other embodiments, a tamping device 412 (FIG. 10A-10B) may comprise multiple components. As shown in FIGS. 10A-10B, the tamping device 412 includes a first longitudinal section 468 at least partially coiled, and a second longitudinal section 472 at least partially coiled. The first longitudinal section 468 may be partially coiled onto a first spool 470, and the second longitudinal section 472 may be partially coiled onto a second spool 474. However, the first and second longitudinal sections 468, 472 may also be guided by first and second external surfaces 476, 478 into the coiled configuration shown. According to FIGS. 10A-10B, the first and second longitudinal sections 468, 472 are mating halves of the tamping device 412 that integrate or mesh together to form a generally circular cross-section as shown in FIG. 10B. Once meshed, the first and second longitudinal sections 468, 472 comprise a generally straight, stiff tube that functions well as a tamping device. The second longitudinal section 472 is advanced or retracted by a main drive gear 480, and the first longitudinal section 468 is simultaneously advanced or retracted by a slave drive gear 482 preferably engaged with the main drive gear 480. The main drive gear 480 is preferably driven by the suture 204 (FIG. 5) as described below with reference to FIGS. 11-12.

Figure 11:
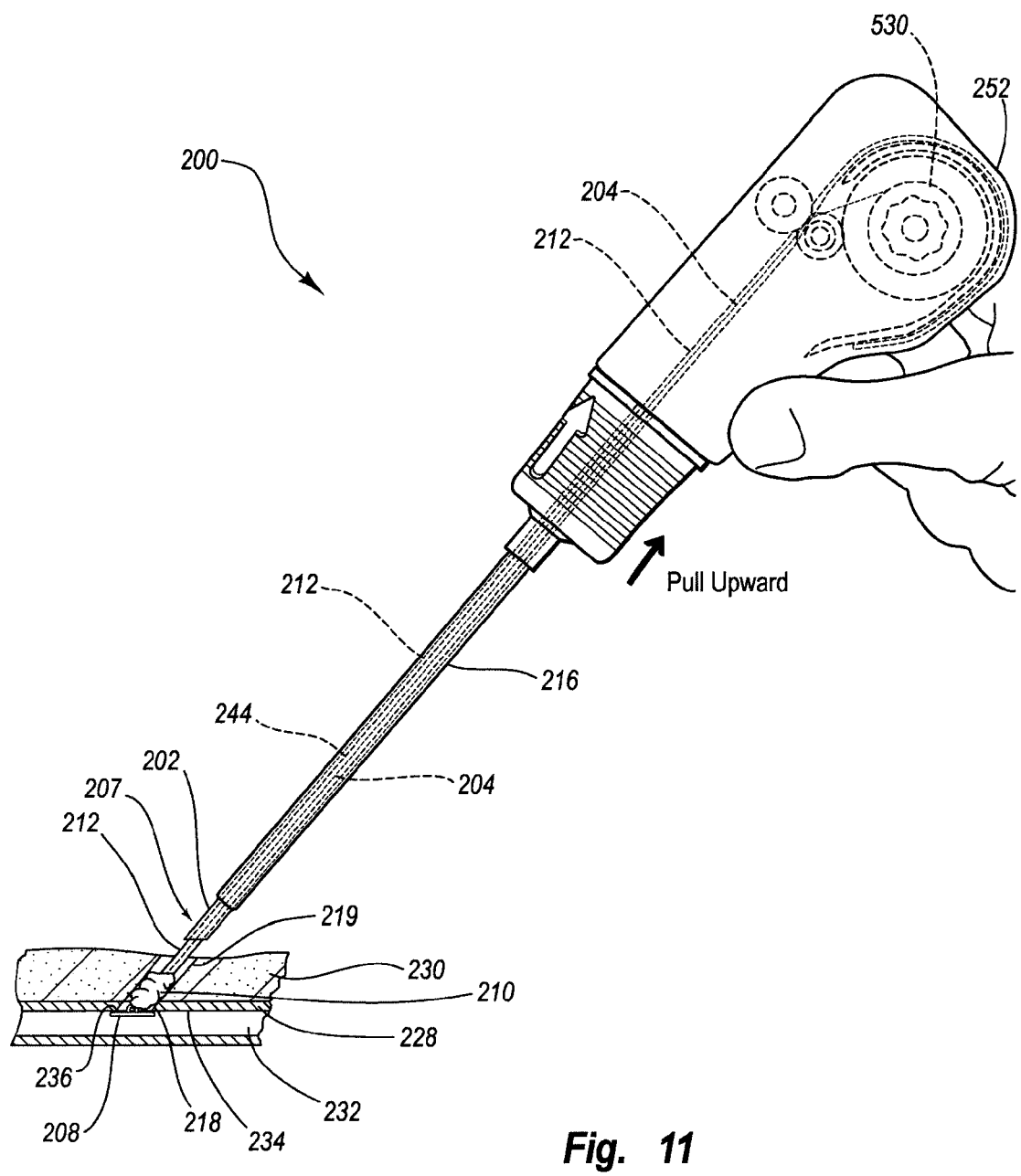
FIG. 11 is a side view of the tissue puncture closure device of FIG. 5 being withdrawn from the artery according to one embodiment of the present invention.

Turning now to FIG. 11, the suture 204 extends through the second section 244 of the tamping device 212 but is not directly connected thereto. Therefore, the suture 204 and tamping device 212 are free to slide past one another. According to the embodiment shown in FIGS. 11-12, as the suture 204 extends into the handle 252 it attaches to an automatic uncoiling mechanism 530 housed within the handle 252.

In practice, the carrier tube 202 of the closure device 200 (containing the closure elements described above) is inserted into the insertion sheath 216, which is already inserted through the artery wall 228. As the closure device 200 and the associated closure elements are inserted into the insertion sheath 216, the anchor 208 passes through and out of the distal end 207 of the insertion sheath 216 and is inserted into the arterial lumen 232. As mentioned above, the anchor 208 is initially arranged substantially parallel with the carrier tube 202 to facilitate insertion of the anchor 208 through the percutaneous incision 219 and into the lumen 232. As the anchor 208 passes out of the insertion sheath 216 and into the lumen 232, the anchor 208 rotates to the position shown in FIG. 11.

With anchor 208 rotated transversely within the lumen 232 as shown in FIG. 11, the closure device 200 and the insertion sheath 216 are withdrawn together, causing the surface 236 of the anchor 208 to bear against the artery wall 234. Further retraction of the closure device 200 and insertion sheath 216 causes the sealing plug 210 to withdraw from the distal end 207 of the carrier tube 202, thereby depositing the plug within the incision or puncture tract 219.

However, unlike previous closure devices that require a separate, manual tamping procedure following the deposition of the sealing plug 210, the closure device 200 of the present invention may automatically tamp the sealing plug 210 with the partially coiled tamping device 212. The closure device 200 uncoils and drives the tamping device 212 toward the sealing plug 212 automatically upon withdrawal of the closure device 200 from the puncture tract 219, tamping the sealing plug 210 toward the anchor 208 as shown in FIG. 11. Therefore, the sealing plug 210 is tamped while the carrier tube 216 is still arranged adjacent to the puncture 218 in the femoral artery 228, reducing or eliminating any gaps that may otherwise occur between the sealing plug 210 and the puncture 218 in the artery wall 228.

In addition, by placing tension on or pulling the suture 204 away from the puncture tract 219, the suture 204 cinches and locks (with a slip knot or the like) the anchor 208 and the sealing plug 210 together, sandwiching the artery wall 228 between the anchor 208 and sealing plug 210. The force exerted by the tamping device 212 and the cinching together of the anchor 208 and sealing plug 210 by the filament 204 also causes the sealing plug 210 to deform radially outward within the puncture tract 219 and function as an anchor on the proximal side of the tissue puncture 218.

Automatically uncoiling (and, depending on the coiled shape of the tamping device 212, shaping) the tamping device 212 toward the sealing plug 210 and/or cinching the seal plug 210 and the anchor 208 may be facilitated by any of a number of mechanisms. For example, the automatic uncoiling mechanism 530 that may be disposed in the handle 252 of the closure device 200 is shown in FIG. 12. According to the embodiment of FIG. 12, retraction of the closure device 200 automatically effects tamping of the sealing plug 210 (FIG. 11). A portion of the force required to retract the closure device 200 from the puncture 218 (FIG. 11) is automatically transduced to an opposite driving force by the automatic uncoiling mechanism 530.

According to the automatic uncoiling mechanism 530 of FIG. 12 (and similarly for FIG. 10A), the suture 204 is connected to and wound about a suture spool 532 (or main drive gear 480 of FIG. 10A). Withdrawal of the closure device 200 (FIG. 11) from the tissue puncture site (if the anchor 208 (FIG. 11) is deployed) causes the suture 204 to unwind from the suture spool 532. The suture spool 532 rotates as the suture 204 unwinds and provides a torsional motive force that may be transduced to a driving or uncoiling force to the tamping device 212.

According to the embodiment of FIG. 12, the torsional motive force provided by the spool 532 is transduced into the driving force for the tamping device 212 by a gear train 534. The gear train 534 includes a first gear 536 arranged coaxially with the suture spool 532. The first gear 536 and the spool 532 may include mating fan surfaces 538, 540, respectively. The mating fan surfaces 538, 540 define a torque-limiting clutch that prevents the transmission of exceptional torsional forces from the spool 532 to the first gear 536 that exceed a predetermined level.

The matching fan surfaces 538, 540 of the first gear 536 and suture spool 532 may be forced into engagement by a biasing member, such as a compressible washer 550, with sufficient force to cause mechanical or frictional engagement of the fan gears surfaces 538, 540, while still permitting mutual rotation about an axis of rotation 552. The fan surfaces 538, 540 are preferably sinusoidally shaped so as to permit slippage between the fan surfaces 538, 540 only when torsional forces reach or exceed a predetermined level. It will be understood, however, that other fan surface shapes may also be used, including, but not limited to, V-shapes, square shapes and flat surfaces. The predetermined torsional force level necessary to overcome the mechanical or frictional engagement of the fan surfaces 538, 540 may be modified by adjusting the frequency or amplitude of the sinusoidally shaped fan faces, by adjusting the biasing force between the fan surfaces 538, 540, or by other methods.

As shown in FIG. 12, the first gear 536 may engage a second gear 542. The first and second gears 536, 542 may engage one another with a frictional fit or with gear teeth. The second gear 542 also engages and uncoils the tamping device 212, which is disposed between the second gear 542 and a roller guide 546. When the spool 532 rotates, the second gear 542 drives the first section 242 of tamping device 212, which is initially coiled, through the shaper 246. The shaper 246, may, however, be arranged downstream of the second gear 542 as well. The shaper 246 may fold certain embodiments of the tamping device 212/312/412 into new stiffer configurations, straighten the tamping device 212/312/412, and/or help mesh multiple tamping device components into a single piece. The second gear 542 also drives the tamping device 212 toward the sealing plug 210 (FIG. 11) and thus advances the sealing plug 210 (FIG. 11) toward the anchor 208 (FIG. 11). It will be understood by the skilled artisan having the benefit of this disclosure that although the shaper 246 (FIG. 5) is shown in FIG. 5 distal of the gears such as second gear 542, the shaper 246 may also be located proximal of the gears.

It may be desirable in some cases to increase the linear velocity of the tamping device 212 relative to the linear velocity at which the closure device 200 may be withdrawn. An increased linear velocity for the tamping device 212 may better assure that the sealing plug 210 (FIG. 11) is forced toward the anchor 208 (FIG. 11) when the closure device 200 is withdrawn from the puncture 218 (FIG. 11). Therefore, according to some embodiments, the gear train 534 may have an overall gear ratio greater than 1:1, and may include additional gears. For example, the gear ratio may range between approximately 2.5:1 and 6.0:1 for some embodiments. According to some embodiments the gear ratio is about 5.0:1.

However, it should be noted that the linear velocity of the tamping device should not be excessively greater than the linear withdrawal velocity of the closure device, as excessive speed could potentially force the sealing plug 210 (FIG. 11) through the tissue puncture 218 (FIG. 11) and into the lumen 232 (FIG. 11). Likewise, an insufficient opposing force against the anchor 208 (FIG. 11) could potentially result in the anchor 208 (FIG. 11) being pulled out of place from within the lumen 232 (FIG. 11). Therefore, according to some uses, the withdrawal force should not exceed approximately 3.5 pounds.

It will be understood by those of skill in the art having the benefit of this disclosure that the drive spool/gear train configuration shown in FIGS. 10A and 12 are exemplary in nature, and not limiting. Any gear configuration may be used to transmit a motive force generated by retraction of the closure device 200 (FIG. 11) to provide an automatic driving force to the sealing plug 210 (FIG. 11). In addition, the torque-limiting clutch may be arranged at any point along the gear train 534 and is not limited to the engagement between the suture spool 532 and the first gear 536.

Operation of the closure device 200 of FIGS. 11-12 is as follows. As the closure device 200 is retracted from the puncture tract 219, a separation force between the handle 252 and the anchor 208 causes the suture 204, which is threaded through the anchor 208, to unwind from and rotate the spool 532. The spool 532 drives the first gear 536 as it rotates via the mating engagement between the fan surfaces 538, 540. As the first gear 536 rotates it drives the second gear 542, and the second gear 542 drives the tamping device 212. The tamping device 212 passes through the shaper 246 where it is arranged into a stiff, straight configuration. The tamping device 212 extends toward and tamps the sealing plug 210. Therefore, as the closing device 200 is retracted from the puncture tract 219, the sealing plug 210 is automatically tamped via the automatic driving mechanism 530. Accordingly, the sealing plug 210 is more likely to create a sufficient arterial seal without gaps between the sealing plug 210 and the anchor 208, as may otherwise occur with a separate manual tamping procedure.

Figure 13:
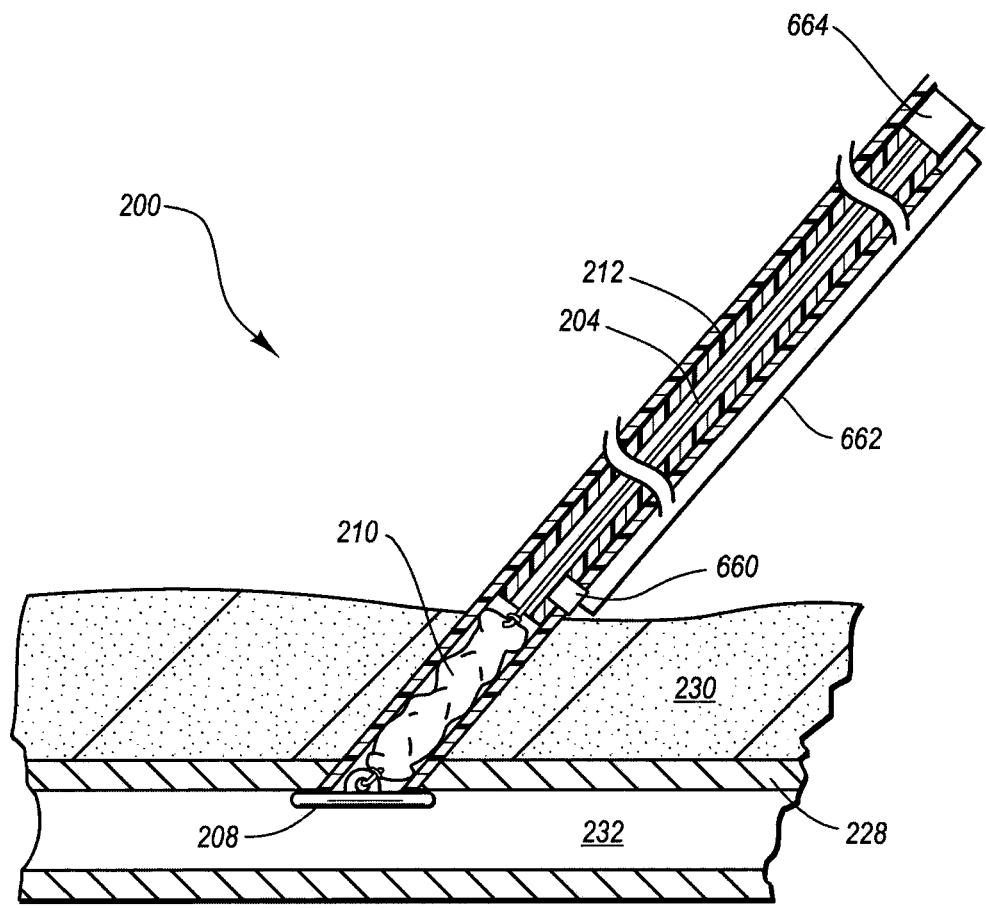
FIG. 13 is an enlarged cross-sectional side view a tissue puncture closure device with an electrical transducer according to one embodiment of the present invention.

Although the embodiments shown and described above illustrate mechanical transducers that may be used to convert forces associated with retraction of the closure tool 200 to an automatic tamping force on the sealing plug 210, other transducers may also be used according to principles of the invention to facilitate automatic tamping of the sealing plug 210. Any means for transducing a motive force in a first direction to a subsequent force in another direction may be used. For example, referring to FIG. 13, electrical switches and/or optical transducers may be used to generate an automatic tamping force upon retraction of the closure tool 200 from a puncture tract. Accordingly, an electrical switch and/or optical sensor 660 may transmit a signal along a communications interface 662 to a motor, servo, solenoid, or other device 664 indicating retraction of the closure device 200. The motor, servo, solenoid, or other device 264 may then provide a tamping force when the retraction signal is received.

Therefore, according to some embodiments the proximal end of the suture 204 may be operatively connected to the electronic switch 660, which is operatively connected to the motor 664 (and/or a power source). Retraction of the closure device 200 may trip the electronic switch 660 and activate the motor 664 to generate a force used to uncoil the tamping device 212 and tamp the sealing plug 210. Similarly, the electronic switch 660 may be or include an optical sensor for detecting and/or measuring withdrawal of the closure device 200 from the tissue puncture and generating a signal indicating withdrawal of the closure device from the tissue puncture. The optical signal may be transduced to an electrical signal, and the electrical signal may be transmitted to the motor 664 (and/or a power source) for generating a driving or tamping force to the sealing plug 210. The motor, servo, solenoid, or other device 664 may be rotary for generating torsional force (which may be transduced to a linear motive force in a manner similar to that described above), or it may be linear for generating a force that may be directly or indirectly applied to the tamping device 212.

The tissue closure devices 200 described above may be particularly useful following an intravascular procedure, such as angioplasty or catheterization. Therefore, the general steps that may be taken for such a procedure are described below, followed by a number of steps that may be taken according to some methods prior to use of the tissue closure device 200.

According to a standard intravascular procedure, a cannula of an instrument, such as an angiographic needle, is inserted through the skin into an artery (e.g. a femoral artery) at the situs for the instrument's insertion. The angiographic needle is held in place and a flexible guidewire is passed through the needle longitudinally into the artery until it reaches a desired depth. Once the guidewire is in place, the angiographic needle is removed, leaving the guidewire in place. A procedure sheath and an arterial dilator are passed over the guidewire, through the puncture or incision, and into the artery. The guidewire and then the dilator are removed, leaving the procedure sheath in place. A catheter or other intravascular instrument is then inserted through the procedure sheath and through the artery to the desired intravascular location, e.g., the situs of an atherosclerotic occlusion. Upon completion of the intravascular procedure (e.g., angioplasty), the catheter is removed, leaving the procedure sheath in place.

The procedure sheath may then be used to facilitate introduction of the closure device 200. First, another guidewire is used to assist in locating the artery. The procedure sheath may then be removed, leaving the guidewire in place. The insertion sheath 216 and a dilator are then inserted along the guidewire, through the percutaneous incision and tissue puncture, and into the artery. The guidewire and dilator are removed, and the insertion sheath 216 is left in place and used for accessing the tissue puncture with the tissue closure device 200 as described above.

The preceding description has been presented only to illustrate and describe exemplary embodiments of invention. It is not intended to be exhaustive or to limit the invention to any precise form disclosed. Many modifications and variations are possible in light of the above teaching. It is intended that the scope of the invention be defined by the following claims.

What is claimed is:

1. A method of sealing a tissue puncture in an internal tissue wall accessible through a percutaneous incision, comprising:
   withdrawing a closure device from the tissue puncture;
   automatically uncoiling a partially coiled tamping device to tamp a sealing plug toward the tissue puncture by transducing a motive force generated by withdrawal of the closure device in a first direction to a tamping force in a second direction;
   wherein the tamping device includes a different cross-sectional shape taken laterally through the tamping device when coiled than when uncoiled.

2. A method of sealing a tissue puncture in an internal tissue wall accessible through a percutaneous incision according to claim 1, wherein the automatically uncoiling further comprises:
   passing the tamping device through a shaper to alter the cross-sectional shape of the tamping device.

3. A method of sealing a tissue puncture in an internal tissue wall accessible through a percutaneous incision according to claim 1, wherein the automatically uncoiling further comprises:
   passing the tamping device through a shaper to alter the cross-sectional shape of the tamping device;
   wherein the altering stiffens the tamping device.

4. A method of sealing a tissue puncture in an internal tissue wall accessible through a percutaneous incision according to claim 1, wherein the transducing further comprises automatically unwinding a filament from a filament spool by deploying an anchor attached to the filament inside the tissue puncture prior to withdrawing the closure device from the tissue puncture.

5. A method of sealing a tissue puncture in an internal tissue wall accessible through a percutaneous incision according to claim 1, wherein the tamping device when uncoiled has a trough cross-sectional shape.

6. A method of sealing a tissue puncture in an internal tissue wall accessible through a percutaneous incision according to claim 1, wherein the tamping device when uncoiled has a cross-sectional shape with a plurality of bends.

7. A method of sealing a tissue puncture in an internal tissue wall accessible through a percutaneous incision, comprising:
   providing a tissue puncture closure device comprising a filament connected at its distal end to an anchor and to a sealing plug located proximal of the anchor for disposition and anchoring about the tissue puncture;
   inserting the tissue puncture closure into the percutaneous incision;
   deploying the anchor into the tissue puncture;
   withdrawing the closure device from the percutaneous incision;
   automatically uncoiling a tamping device upon withdrawal of the closure device from the internal tissue wall puncture;
   reshaping a cross-section of the tamping device from a flat cross-sectional shape to a non-flat cross-sectional shape;
   tamping the sealing plug toward the anchor.

8. A method according to claim 7, wherein the reshaping includes contacting the tamping device with a shaper.

9. A method according to claim 7, wherein the reshaping includes changing the cross-section of the tamping device from a flat cross-section to a folded cross-section.

10. A method according to claim 9, wherein the folded cross-section includes a trough shape.

11. A method according to claim 7, wherein the tamping device includes at least one recess along its length, and the reshaping includes bending the tamping device at the recess.

12. A method of treating a vascular incision, comprising:
   providing a vascular closure device having a filament, an anchor, a sealing plug, and an at least partially coiled tamping device, the filament extending from a first end to a second end of the closure device, the anchor attached to the filament at the second end of the device, the sealing plug slidingly attached to the filament adjacent to the anchor, and the tamping device having a distal end arranged adjacent to the sealing plug and a cross-section taken laterally through the tamping device;
   inserting the anchor through the vascular incision at a location distal of the vascular incision;
   withdrawing the vascular closure device to dispose the sealing plug proximal of the vascular incision;
   uncoiling the tamping device to compact the sealing plug toward the anchor, wherein uncoiling the tamping device includes changing a shape of the cross-section of the tamping device.

13. A method according to claim 12, wherein changing a cross-sectional shape of the tamping device includes changing from a flat cross-section to a trough shaped cross-section.

14. A method according to claim 12, wherein changing a cross-sectional shape of the tamping device includes folding the tamping device.

15. A method according to claim 12, wherein the vascular closure device further includes a shaper positioned at the first end, wherein uncoiling the tamping device includes contacting the tamping device with the shaper to change the cross-sectional shape of the tamping device.

16. A method according to claim 15, wherein the shaper is positioned distal of a coiled portion of the tamping member.

17. A method according to claim 15, wherein a portion of the tamping device proximal of the shaper comprises a curved, flexible configuration and a portion of the tamping device distal of the shaper comprises a straight, stiff configuration.

18. A method according to claim 12, wherein changing a cross-sectional shape of the tamping device includes changing from a flat cross-sectional shape to a one of: a U-shaped, a V-shaped, or a closed polygonal shaped cross-section.

19. A method according to claim 12, wherein the filament is coiled around a spool, wherein rotating the spool by unwinding the filament rotates at least one gear to unwind the tamping device.

20. A method according to claim 12, wherein the vascular closure device further comprises an automatic unwinding device for unwinding the tamping device in response to retraction of the tissue puncture closure device from the tissue puncture.

21. A method of sealing a tissue puncture in an internal tissue wall accessible through a percutaneous incision, comprising:
   withdrawing a closure device from the tissue puncture;
   automatically uncoiling a partially coiled tamping device to tamp a sealing plug toward the tissue puncture by transducing a motive force generated by withdrawal of the closure device in a first direction to a tamping force in a second direction;
   wherein the tamping device includes a different cross-sectional shape when coiled than when uncoiled;
   wherein the automatically uncoiling further comprises passing the tamping device through a shaper to alter the cross-sectional shape of the tamping device, wherein the altering stiffens the tamping device.

22. A method of sealing a tissue puncture in an internal tissue wall accessible through a percutaneous incision, comprising:
   withdrawing a closure device from the tissue puncture;
   automatically uncoiling a partially coiled tamping device to tamp a sealing plug toward the tissue puncture by transducing a motive force generated by withdrawal of the closure device in a first direction to a tamping force in a second direction;
   wherein the tamping device includes a different cross-sectional shape when coiled than when uncoiled;
   wherein the tamping device when uncoiled has a cross-sectional shape with a plurality of bends.

23. A method of sealing a tissue puncture in an internal tissue wall accessible through a percutaneous incision, comprising:
   providing a tissue puncture closure device comprising a filament connected at its distal end to an anchor and to a sealing plug located proximal of the anchor for disposition and anchoring about the tissue puncture;
   inserting the tissue puncture closure into the percutaneous incision;
   deploying the anchor into the tissue puncture;
   withdrawing the closure device from the percutaneous incision;
   automatically uncoiling a tamping device upon withdrawal of the closure device from the internal tissue wall puncture;
   reshaping a cross-section of the tamping device;
   tamping the sealing plug toward the anchor;
   wherein the reshaping includes changing the cross-section of the tamping device from a flat cross-section to a folded cross-section.

24. A method of sealing a tissue puncture in an internal tissue wall accessible through a percutaneous incision, comprising:
   providing a tissue puncture closure device comprising a filament connected at its distal end to an anchor and to a sealing plug located proximal of the anchor for disposition and anchoring about the tissue puncture;
   inserting the tissue puncture closure into the percutaneous incision;
   deploying the anchor into the tissue puncture;
   withdrawing the closure device from the percutaneous incision;
   automatically uncoiling a tamping device upon withdrawal of the closure device from the internal tissue wall puncture;
   reshaping a cross-section of the tamping device;
   tamping the sealing plug toward the anchor;
   wherein the tamping device includes at least one recess along its length, and the reshaping includes bending the tamping device at the recess.

25. A method of treating a vascular incision, comprising:
   providing a vascular closure device having a filament, an anchor, a sealing plug, and an at least partially coiled tamping device, the filament extending from a first end to a second end of the closure device, the anchor attached to the filament at the second end of the device, the sealing plug slidingly attached to the filament adjacent to the anchor, and the tamping device having a distal end arranged adjacent to the sealing plug;
   inserting the anchor through the vascular incision at a location distal of the vascular incision;
   withdrawing the vascular closure device to dispose the sealing plug proximal of the vascular incision;
   uncoiling the tamping device to compact the sealing plug toward the anchor, wherein uncoiling the tamping device includes changing a cross-sectional shape of the tamping device;
   wherein changing a cross-sectional shape of the tamping device includes folding the tamping device.

26. A method of treating a vascular incision, comprising:
   providing a vascular closure device having a filament, an anchor, a sealing plug, and an at least partially coiled tamping device, the filament extending from a first end to a second end of the closure device, the anchor attached to the filament at the second end of the device, the sealing plug slidingly attached to the filament adjacent to the anchor, and the tamping device having a distal end arranged adjacent to the sealing plug;
   inserting the anchor through the vascular incision at a location distal of the vascular incision;
   withdrawing the vascular closure device to dispose the sealing plug proximal of the vascular incision;
   uncoiling the tamping device to compact the sealing plug toward the anchor, wherein uncoiling the tamping device includes changing a cross-sectional shape of the tamping device;

wherein changing a cross-sectional shape of the tamping device includes changing from a flat cross-sectional shape to a one of: a U-shaped, a V-shaped, or a closed polygonal shaped cross-section.

27. A method of treating a vascular incision, comprising:
providing a vascular closure device having a filament, an anchor, a sealing plug, and an at least partially coiled tamping device, the filament extending from a first end to a second end of the closure device, the anchor attached to the filament at the second end of the device, the sealing plug slidingly attached to the filament adjacent to the anchor, and the tamping device having a distal end arranged adjacent to the sealing plug;
inserting the anchor through the vascular incision at a location distal of the vascular incision;
withdrawing the vascular closure device to dispose the sealing plug proximal of the vascular incision;
uncoiling the tamping device to compact the sealing plug toward the anchor, wherein uncoiling the tamping device includes changing a cross-sectional shape of the tamping device;
wherein the vascular closure device further includes a shaper positioned at the first end, a portion of the tamping device proximal of the shaper comprises a curved, flexible configuration, and a portion of the tamping device distal of the shaper comprises a straight, stiff configuration, and uncoiling the tamping device includes contacting the tamping device with the shaper to change the cross-sectional shape of the tamping device.

* * * * *